(12) United States Patent
Zhao et al.

(10) Patent No.: US 11,701,338 B2
(45) Date of Patent: Jul. 18, 2023

(54) USE OF GTSO THAL IN MANUFACTURING MEDICAMENT FOR PROMOTION OF MS-275 TO CROSS BLOOD-BRAIN BARRIER

(71) Applicant: Northwest Institute of Plateau Biology, Chinese Academy of Sciences, Xining (CN)

(72) Inventors: Xiaohui Zhao, Xining (CN); Ting Zhang, Xining (CN); Huilan Yue, Xining (CN); Jihong Tao, Xining (CN); Wenjing Jia, Xining (CN); Guoying Zhou, Xining (CN); Lixin Wei, Xining (CN); Chen Chen, Xining (CN)

(73) Assignee: Northwest Institute of Plateau Biology, Chinese Academy of Sciences, Xining (CN)

( * ) Notice: Subject to any disclaimer, the term of this patent is extended or adjusted under 35 U.S.C. 154(b) by 222 days.

(21) Appl. No.: 16/987,800

(22) Filed: Aug. 7, 2020

(65) Prior Publication Data

US 2021/0290588 A1 Sep. 23, 2021

(30) Foreign Application Priority Data

Mar. 23, 2020 (CN) .......................... 202010206060.4

(51) Int. Cl.
*A61K 31/305* (2006.01)
*A61K 31/4406* (2006.01)
*A61K 47/12* (2006.01)
*A61K 47/26* (2006.01)
*A61K 47/38* (2006.01)
*A61K 9/00* (2006.01)
*A61K 9/14* (2006.01)
*A61K 9/48* (2006.01)

(52) U.S. Cl.
CPC ........ *A61K 31/305* (2013.01); *A61K 31/4406* (2013.01); *A61K 47/12* (2013.01); *A61K 47/26* (2013.01); *A61K 47/38* (2013.01); *A61K 9/0019* (2013.01); *A61K 9/14* (2013.01); *A61K 9/48* (2013.01)

(58) Field of Classification Search
CPC .................................................... A61K 31/305
See application file for complete search history.

(56) References Cited

PUBLICATIONS

Patel, CNS Drugs, 2009;23(1):35-58.*

* cited by examiner

*Primary Examiner* — Nizal S Chandrakumar
(74) *Attorney, Agent, or Firm* — Pilloff Passino & Cosenza LLP; Sean A. Passino; Rachel K. Pilloff

(57) ABSTRACT

The present invention relates to use of gTso thal in manufacturing a medicament for the promotion of MS-275 to cross the blood-brain barrier (BBB), and belongs to the technical field of pharmaceutical preparation. Administration of the medicament manufactured by the use of the present invention in combination with MS-275 significantly increases MS-275 to cross the BBB into the brain tissue, and prominently promotes the accumulation of MS-275 therein.

12 Claims, 2 Drawing Sheets

USE OF GTSO THAL IN MANUFACTURING MEDICAMENT FOR PROMOTION OF MS-275 TO CROSS BLOOD-BRAIN BARRIER

TECHNICAL FIELD

The present invention relates to the technical field of pharmaceutical preparation, and in particular to use of gTso thal in manufacturing a medicament for the promotion of MS-275 to cross the blood-brain barrier (BBB).

BACKGROUND

Tibetan drug gTso thal is a core preparation and typical representative of Tibetan medicine, and main component thereof is mercury sulfide. gTso thal is principally and widely used in compound preparations of Tibetan medicine in the form of adjuvant; the drug is still in use today after thousands of years of clinical use. In theory of Tibetan medicine, gTso thal plays a role in enhancing the efficacy of all drugs in compound drugs and is an essential adjuvant to prepare treasure drugs. Preparations with gTso thal tend to play unique roles in the treatment of stroke, paralysis, hypertension, nervous system diseases, cardiovascular disorders, hepatobiliary and gastrointestinal diseases, tumors, etc.

MS-275 is a synthetic benzamide histone deacetylase inhibitor. So far, it has been indicated that MS-275 can induce tumor cell proliferation, arrest, differentiation, and apoptosis, and act selectively on tumor cells. It has been demonstrated that MS-275 exhibits antiproliferative activity and has excellent therapeutic effects on leukemia and solid tumors, including breast carcinoma, myeloma, colon carcinoma, lung carcinoma, etc. In recent years, research on MS-275 in the treatment of nervous system diseases has drawn more and more attentions. It has been demonstrated that MS-275 has therapeutical effects on such neurodegenerative diseases as cognitive dysfunction, Parkinson disease, and dementia, and that histone deacetylase is a target of MS-275. BBB, present in the brain, is a natural barrier that separates blood from central nervous system (CNS); the BBB maintains a stable intracerebral environment, blocks the invasion of harmful substances, and protects the brain from external injury. However, the presence thereof leads to the fact that a number of medicaments for the treatment of cerebral diseases fail to enter the brain to work. Limited by the BBB, MS-275 fails to enter the brain efficiently; after oral or intravenous administration, only around 15% of the dosage of MS-275 crosses the BBB into the brain, resulting in a poor therapeutic effect of MS-275. Direct intracerebral administration can substantially improve efficacy, but such route of administration is limited clinically because of high difficulty and additional damage to patients.

SUMMARY

An objective of the present invention is to provide use of gTso thal in manufacturing a medicament for the promotion of MS-275 to cross the BBB. Administration of the medicament manufactured by the use of the present invention in combination with MS-275 significantly increases MS-275 to cross the BBB into the brain tissue, and prominently promotes the accumulation of MS-275 therein.

The present invention provides use of gTso thal in manufacturing a medicament for the promotion of MS-275 to cross the BBB.

Preferably, the gTso thal and MS-275 are mixed in a mass ratio of (1-10):(0.1-200,000) in the use.

Preferably, the gTso thal and MS-275 are mixed in a mass ratio of (1-10):(10-5,000) in the use.

Preferably, the pharmaceutical dosage form includes injection, powder injection, granule, or capsule.

Preferably, the medicament further includes pharmaceutically acceptable excipients, and the excipients include: sodium carboxymethylcellulose (CMC-Na) in the injection; glucose, lactose, and/or mannitol in the powder injection; starch, lactose, magnesium stearate, aerosil, and/or polysorbate 80 in the capsule; starch, lactose, dextrin, and/or hydroxypropyl methyl cellulose (HPMC) in the granule.

The present invention provides the use of gTso thal in manufacturing the medicament for the promotion of MS-275 to cross the BBB. Administration of the medicament manufactured by the use of the present invention in combination with MS-275 significantly increases MS-275 to cross the BBB into the brain tissue, and prominently promotes the accumulation of MS-275 therein.

DETAILED DESCRIPTION

Figure 1:
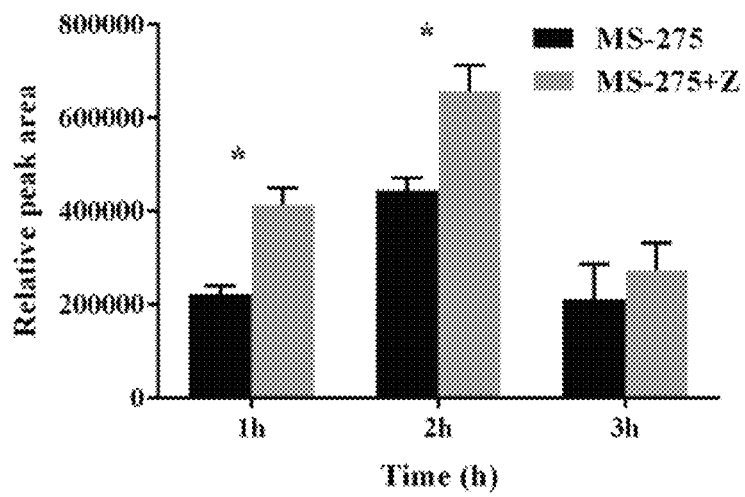
FIG. 1 illustrates the results of the promotion of MS-275 to enter the brain tissue at different time points after administration of gTso thal in combination with MS-275 provided in Example 1 of the present invention.

The present invention provides use of gTso thal in manufacturing the medicament for the promotion of MS-275 to cross the BBB. Sources of the gTso thal are not particularly limited in the present invention, as long as commercially available gTso thal used is well known to those skilled in the art. gTso thal has a long history of clinical use in traditional Tibetan medicine, but there are few studies and reports on how gTso thal plays a role in a compound preparation, how gTso thal works, and what mechanism of action thereof is; mechanisms of action of mercury sulfide medicaments in traditional Chinese and Indian medicine are seldom investigated, and it is even controversial whether these medicaments are effective. Administration of the medicament manufactured by the use of the present invention in combination with MS-275 significantly increases MS-275 to cross the BBB into the brain tissue, and prominently promotes the accumulation of MS-275 therein.

In the present invention, gTso thal and MS-275 are preferably mixed in a mass ratio of (1-10):(0.1-200,000), and more preferably (1-10):(10-5,000) in the use.

In the present invention, the pharmaceutical dosage form includes injection, powder injection, granule, or capsule. When the medicament provided by the present invention is in a form of injection, a method for manufacturing the medicament provided by the present invention preferably includes the following steps: mixing gTso thal with PBS or normal saline solution and ultrasonically dissolving to obtain the medicament. In the present invention, the sonication preferably lasts for 5-30 min. When the medicament provided by the present invention is in a form of injection, a method for manufacturing MS-275 injection preferably includes the following steps: mixing MS-275 with dimethyl sulfoxide (DMSO) or normal saline solution (V:V=1:9) and ultrasonically dissolving. In the present invention, the sonication more preferably lasts for 10 min.

In the present invention, the medicament further includes pharmaceutically acceptable excipients, and the excipients preferably include: CMC-Na in the injection; glucose, lactose, and/or mannitol in the powder injection; starch, lactose, magnesium stearate, aerosil, and/or polysorbate 80 in the capsule; starch, lactose, dextrin, and/or HPMC in the granule.

In the present invention, when the medicament is administered in combination with MS-275, the medicament is preferably administered 1-3 h in advance, and the route of administration preferably includes intraperitoneal injection or intragastric administration. In the present invention, preferably, gTso thal has an effective dose of 0.0005-1 mg/kg of body weight, and more preferably 0.005 mg/kg of body weight in the medicament. In the present invention, the MS-275 is preferably administered at a dose of 1-30 mg/kg of body weight, and more preferably 10 mg/kg of body weight. In the present invention, in case of long-term administration, gTso thal is preferably administered every other day or every 2-5 days.

The use of gTso thal in manufacturing the medicament for the promotion of MS-275 to cross the BBB provided by the present invention will be further described in detail below in conjunction with examples, and the technical solutions of the present invention include but are not limited to the following examples.

Example 1

Preparation of Medicament

Dosages of MS-275 and gTso thal (Z) were 20.0 and 0.005 mg/kg, respectively. MS-275 solution was prepared as follows: dissolving MS-275 (quantum sufficit, q.s.) in dimethyl sulfoxide (DMSO) and phosphate buffered saline (PBS) (V:V=1:9), and sonicating for 10 min to dissolve fully for use. gTso thal solution was prepared as follows: ultrasonically dissolving gTso thal in PBS.

Single-Dose Administration

Grouping and administration: Mice were randomized into 18 groups of 3 animals each (3 parallel groups for each animal group) as follows: MS-275 alone 1 h groups, MS-275 alone 2 h groups, MS-275 alone 3 h groups, MS-275+Z 1 h groups, MS-275+Z 2 h groups, and MS-275+Z 3 h groups, respectively. Mice in MS-275+Z groups were intraperitoneally administered 0.3 ml of gTso thal in advance, and after 3 h, mice in all groups were intraperitoneally administered MS-275 at the same dose as gTso thal.

Sample collection: At 1, 2, and 3 h after administration, mice were subjected to cardiac perfusion with PBS at different time points; brain tissues thereof were extracted, placed in centrifuge tubes, and cryopreserved in a refrigerator at −20° C.

Long-Term Administration

Grouping and administration: Mice were randomized into 6 groups of 3 animals each (3 parallel groups for each animal group) as follows: MS-275 alone groups and MS-275+Z groups, respectively. Mice in MS-275+Z groups were intraperitoneally administered gTso thal every three days; mice in all groups were intraperitoneally administered MS-275 at the same dose as gTso thal daily for seven consecutive days.

Sample collection: At 1 h after the last administration, mice were subjected to cardiac perfusion with PBS. Brain tissues thereof were extracted, placed in centrifuge tubes, and cryopreserved in a refrigerator at −20° C.

Sample Pretreatment

Brain tissue sample pretreatment: Brain tissue was homogenized with DMSO. After sonication for 30 min and centrifugation for 5 min (at 5,500 rpm at 4° C.), supernatant was collected; the foregoing steps were repeated thrice and extracts were combined. The combined extract was concentrated under reduced pressure and evaporated to dryness in a rotary evaporator. Residues were collected and dissolved in 4 ml of methanol ultrasonically; then, the resulting solution was filtered through an organic membrane into a centrifuge tube and assayed by liquid chromatography-mass spectrometry (LC-MS).

Chromatographic and Mass Spectrometric (MS) Conditions

Chromatographic conditions of MS-275 were as follows: mobile phase 40% methanol:water (40:60), flow rate 0.30 mL/min, column temperature 40° C., and injection volume 10 µL. MS conditions were as follows: electrospray ionization (EMI) (TurboIonSpray), multiple reaction monitoring (MRM) mode, IonSpray voltage 5,500V, TurboIonSpray temperature (TEM) 550° C., curtain gas (CUR) 30 psi, collision gas (CAD) 9 psi, nebulizer gas (GS1) 55 psi, and heater gas (GS2) 55 psi; mass to charge ion (m/z) of MS-275, 377.4/359.2 and 377.4/269.2; declustering potential (DP) 75, entrance potential (EP) 10, collision energy (CE) 27, and collision cell exit potential (CXP) 13.

Figure 2:
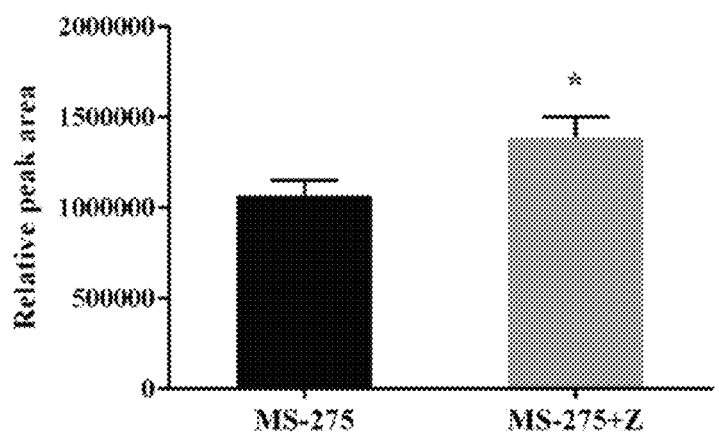
FIG. 2 illustrates the results of the promotion of MS-275 to enter the brain tissue at 7 days after administration of gTso thal in combination with MS-275 provided in Example 1 of the present invention.

Results are shown in FIGS. 1 and 2. Specifically, FIG. 1 illustrates the results of the promotion of MS-275 to enter the brain tissue at different time points after administration of gTso thal in combination with MS-275; FIG. 2 illustrates the results of the promotion of MS-275 to enter the brain tissue at 7 days after administration of gTso thal in combination with MS-275. From FIG. 1, administration of gTso thal in combination with MS-275 can significantly increase MS-275 to cross the BBB into the brain tissue. At 1, 2, and 3 h after administration, the dosage increases by 85.87±6.84%, 47.33±7.56%, and 41.21±32.93% (mean±SD) in MS-275+Z groups compared with MS-275 alone groups at different time points, respectively. From FIG. 2, long-term administration of gTso thal in combination with MS-275 can prominently promote the accumulation of MS-275 in the brain tissue. At 7 days after administration, the relative dosage of MS-275 in the brain tissue increases by 29.93±4.71% in MS-275+Z groups compared with MS-275 alone groups.

Example 2

Preparation of Medicament

Dosages of MS-275 and gTso thal (Z) were 15.0 and 0.001 mg/kg, respectively. MS-275 solution was prepared as follows: dissolving MS-275 (q.s.) in DMSO and PBS (V:V=1:9), and sonicating for 10 min to dissolve fully for use. gTso thal solution was prepared as follows: ultrasonically dissolving gTso thal in PBS.

Single-Dose Administration

Grouping and administration: Mice were randomized into 18 groups of 3 animals each (3 parallel groups for each animal group) as follows: MS-275 alone 1 h groups, MS-275 alone 2 h groups, MS-275 alone 3 h groups, MS-275+Z 1 h groups, MS-275+Z 2 h groups, and MS-275+Z 3 h groups, respectively. Mice in MS-275+Z groups were intraperitoneally administered 0.3 ml of gTso thal in advance, and after 3 h, mice in all groups were intraperitoneally administered MS-275 at the same dose as gTso thal.

Sample collection: At 1, 2, and 3 h after administration, mice were subjected to cardiac perfusion with PBS at different time points; brain tissues thereof were extracted, placed in centrifuge tubes, and cryopreserved in a refrigerator at −20° C.

Long-Term Administration

Grouping and administration: Mice were randomized into 6 groups of 3 animals each (3 parallel groups for each animal group) as follows: MS-275 alone groups and MS-275+Z groups, respectively. Mice in MS-275+Z groups were intraperitoneally administered gTso thal every three days; mice in all groups were intraperitoneally administered MS-275 at the same dose as gTso thal daily for seven consecutive days.

Sample collection: At 1 h after the last administration, mice were subjected to cardiac perfusion with PBS. Brain tissues thereof were extracted, placed in centrifuge tubes, and cryopreserved in a refrigerator at −20° C.

Sample Pretreatment

Brain tissue sample pretreatment: Brain tissue was homogenized with DMSO. After sonication for 30 min and centrifugation for 5 min (at 5,500 rpm at 4° C.), supernatant was collected; the foregoing steps were repeated thrice and extracts were combined. The combined extract was concentrated under reduced pressure and evaporated to dryness in a rotary evaporator. Residues were collected and dissolved in 4 ml of methanol ultrasonically; then, the resulting solution was filtered through an organic membrane into a centrifuge tube and assayed by LC-MS.

Chromatographic and MS Conditions

Chromatographic conditions of MS-275 were as follows: mobile phase 40% methanol:water (40:60), flow rate 0.30 mL/min, column temperature 40° C., and injection volume 10 μL. MS conditions were as follows: EMI (TurboIonSpray), MRM mode, IonSpray voltage 5,500V, TEM 550° C., CUR 30 psi, CAD 9 psi, GS1 55 psi, and GS2 55 psi; m/z of MS-275, 377.4/359.2 and 377.4/269.2; DP 75, EP 10, CE 27, and CXP 13.

Figure 3:
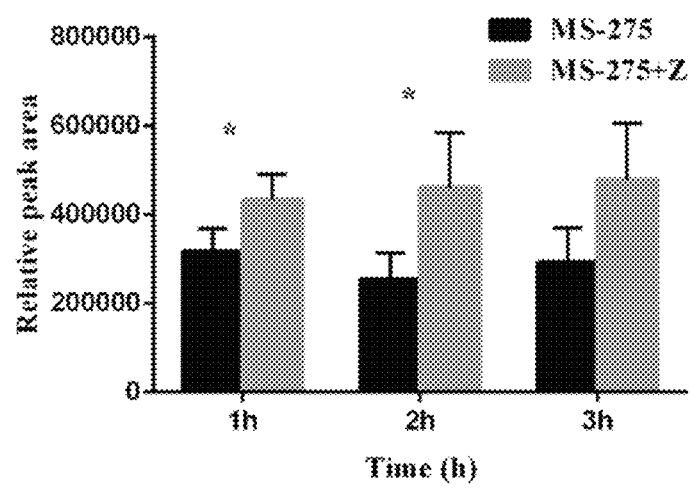
FIG. 3 illustrates the results of the promotion of MS-275 to enter the brain tissue at different time points after administration of gTso thal in combination with MS-275 provided in Example 2 of the present invention.
Figure 4:
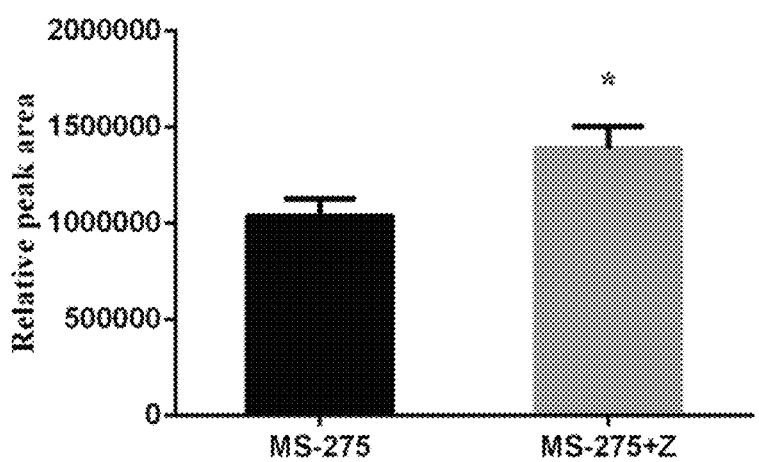
FIG. 4 illustrates the results of the promotion of MS-275 to enter the brain tissue at 7 days after administration of gTso thal in combination with MS-275 provided in Example 2 of the present invention.

Results are shown in FIGS. 3 and 4. Specifically, FIG. 3 illustrates the results of the promotion of MS-275 to enter the brain tissue at different time points after administration of gTso thal in combination with MS-275; FIG. 4 illustrates the results of the promotion of MS-275 to enter the brain tissue at 7 days after administration of gTso thal in combination with MS-275. From FIG. 3, administration of gTso thal in combination with MS-275 can significantly increase MS-275 to cross the BBB into the brain tissue. At 1, 2, and 3 h after administration, the dosage increases by 80.61±11.42%, 64.87±19.49%, and 38.18±25.86% (mean±SD) in MS-275+Z groups compared with MS-275 alone groups at different time points, respectively. From FIG. 4, long-term administration of gTso thal in combination with MS-275 can prominently promote the accumulation of MS-275 in the brain tissue. At 7 days after administration, the relative dosage of MS-275 in the brain tissue increases by 34.13±2.62% in MS-275+Z groups compared with MS-275 alone groups.

The foregoing descriptions are merely preferred examples of the present invention, and it should be noted that various modifications and variations can be made by those skilled in the art without departing from the principles of the present invention and are within the scope of the invention.

What is claimed is:

1. A medicament for the promotion of MS-275 to cross the blood-brain barrier (BBB), comprising gTso thal and pharmaceutically acceptable excipients.

2. The medicament according to claim 1, wherein the pharmaceutical dosage form comprises injection, powder injection, granule, or capsule.

3. The medicament according to claim 1, wherein the pharmaceutically acceptable excipients comprise: sodium carboxymethylcellulose (CMC-Na) in the injection; glucose, lactose, and/or maitol in the powder injection; starch, actose, magnesium stearate, aerosil, and/or polysorbate 80 in the capsule; starch, lactose, dextrin, and/or hydroxypropyl methyl cellulose (HPMC) in the granule.

4. A method for manufacturing a medicament for the promotion of MS-275 to cross the BBB by gTso thal, comprising the following steps: mixing gTso thal with pharmaceutically acceptable excipient(s) to manufacture the medicament.

5. A method for promoting MS-275 to cross by the blood-brain barrier (BBB) of a patient in need of MS-275 treatment, comprising administering a medicament comprising gTso thal and one or more pharmaceutically acceptable excipients, in combination with MS-275.

6. The method according to claim 5, wherein gTso thal and MS-275 are mixed in a mass ratio of (1-10):(0.1-200,000) when administered concomitantly.

7. The method according to claim 5, wherein gTso thal and MS-275 are mixed in a mass ratio of (1-10):(10-5,000) when administered concomitantly.

8. The method according to claim 5, wherein the medicament is administered 1-3 h in advance when the medicament is administered in advance of MS-275.

9. The method according to claim 5, wherein the route of administration comprises intraperitoneal injection or intragastric administration.

10. The method according to claim 5, wherein the gTso thal has an effective dose of 0.0005-1 mg/kg of body weight of the patient in the medicament.

11. The method according to claim 5, wherein the MS-275 is administered at a dose of 1-30 mg/kg of body weight of the patient.

12. The method according to claim 5, wherein the medicament is administered every other day or every 2-5 days.

* * * * *